United States Patent [19]

Cosyns et al.

[11] 4,392,002
[45] Jul. 5, 1983

[54] PROCESS FOR UPGRADING OLEFINIC $C_4$ CUTS

[75] Inventors: Jean Cosyns, Maule; Bernard Juguin; Jean-François Le Page, both of Rueil Malmaison; Jean Miquel, Paris, all of France

[73] Assignee: Institut Francais du Petrole, Ruell-Malmaison, France

[21] Appl. No.: 311,828

[22] Filed: Oct. 16, 1981

[30] Foreign Application Priority Data

Oct. 16, 1980 [FR] France .................................. 80 22204

[51] Int. Cl.³ ........................... C07C 2/08; C07C 2/58
[52] U.S. Cl. ................................. 585/329; 585/331; 585/332
[58] Field of Search ...................... 585/329, 331, 332

[56] References Cited

U.S. PATENT DOCUMENTS 4,268,701  5/1981  Vu et al. .............................. 585/329

Primary Examiner—Curtis R. Davis
Attorney, Agent, or Firm—Millen & White

[57] ABSTRACT

A $C_4$ cut is upgraded according to the following steps:
(a) the dried $C_4$ cut is polymerized in the presence of fluorinated alumina, boron-alumina or silica-alumina, to convert at least 95% of isobutene to dimers and trimers, the conversion of the normal butenes being at most 3%,
(b) the whole polymerization effluent is hydro-isomerized in the presence of a group VIII metal catalyst, to isomerize at least 90% of the 1-butene of said effluent,
(c) the hydro-isomerization effluent is fractionated and a resultant fraction is alkylated.

Resultant alkylate and mixture of dimers and trimers can be mixed and used as gasoline.

9 Claims, 1 Drawing Figure

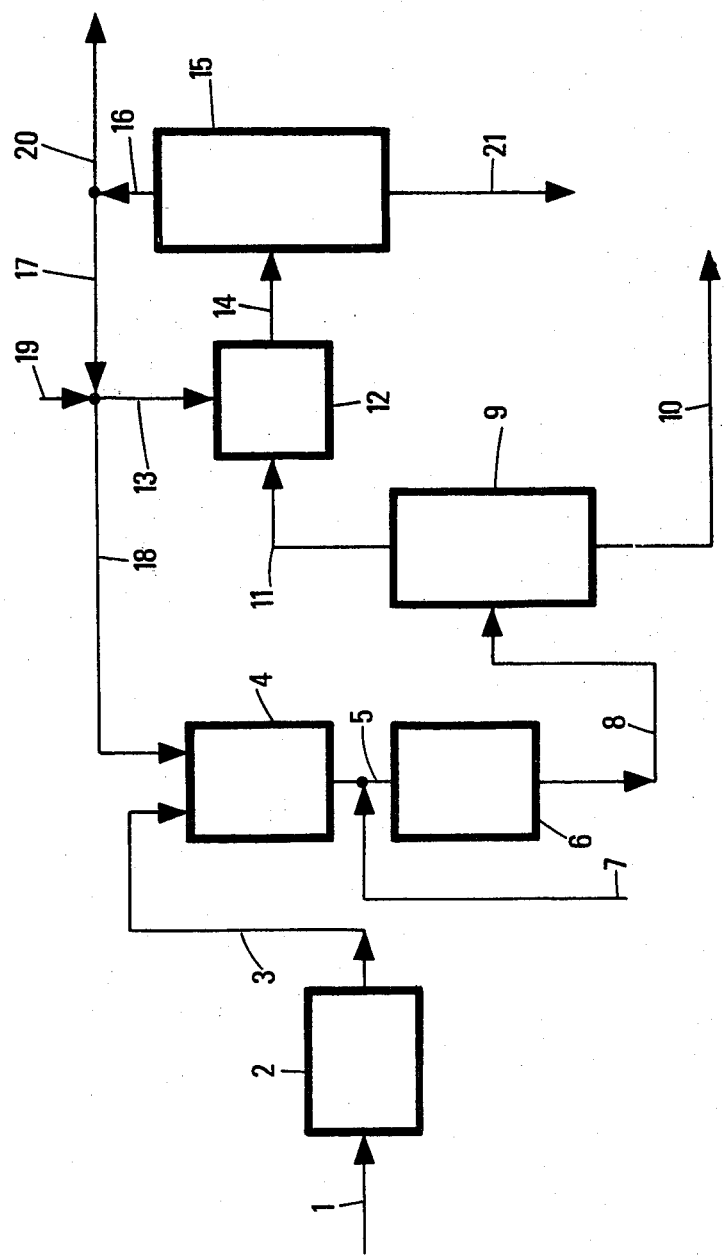

PROCESS FOR UPGRADING OLEFINIC C4 CUTS

BACKGROUND OF THE INVENTION

The development of various processes for the steam-cracking and catalytic cracking of naphthas and gas oils puts on the market a $C_4$ cut, which, after butadiene extraction, essentially contains a mixture of butenes, isobutene, butane and isobutane which must be upgraded.

The olefins, butenes and isobutene, can be used in the petrochemical synthesis of more elaborate products (alcohols, aldehydes, acids, nitriles, etc.); however the available amounts of these $C_4$ cuts are, as a rule, too large or, at least, can become too large for this upgrading method alone.

A second upgrading method consists of recycling the $C_4$ cut to the cracking (steam-cracking) or catalytic cracking unit, after olefin hydrogenation; however the isobutane of the hydrogenated cut, which amounts to more than 50% by weight of said cut, does not lead to sufficiently valuable ethylene yields and also leads to a substantial production of methane usable only as fuel.

A third upgrading method for said $C_4$ cut consists, after hydrogenation of the cut, of separating n-butane from isobutane by distillation and recycling only n-butane to the steam-cracking unit, isobutane being left apart for other more advantageous uses, such as alkylation for the production of isoparaffinic gasolines. However the yields of ethylene and propylene, in such a steam-cracking, do not exceed 38 and 20% b.w. respectively, and the production of methane is about 25% b.w.

A fourth method to upgrade the $C_4$ cut consists of alkylating the olefins of the cut with the isobutane contained therein to maximize the gasoline yield. However, in the alkylation step, the behaviour of isobutene is not so favorable as that of the butenes as concerns the production of high octane gasoline; as a matter of fact, the Research (or Clear) octane numbers of the alkylates obtained from normal butenes are higher than those obtained from isobutene.

This fourth method can be improved, in a first time by first subjecting the $C_4$ cut to polymerization while limiting as much as possible the global conversion of the normal butenes of the cut to less than 10% and converting more than 90% of isobutene (preferably, more than 92%); this hydrocarbon is essentially converted to isobutene dimers and trimers; thereafter, the so-obtained product is fractionated into a first fraction which is fed to the alkylation unit, and, a second fraction which is fed to the gasoline pool after partial or total hydrogenation. The first fraction, which is fed to the alkylation unit, contains, in major part, butane and isobutane as well as the butenes which have not reacted during polymerization. A process of this type is described in the British patent application No. 2,017,746.

SUMMARY OF THE INVENTION

The present invention is an improvement of the process disclosed in British patent application No. 2,017,746 for upgrading the $C_4$ cut and comprises subjecting the olefinic $C_4$ cut, not just to a polymerization reaction, such as hereinabove described, but to the coupling of a polymerization reaction with an isomerization reaction, said coupling not only providing for a selective conversion of isobutene to $C_8$ dimers and $C_{12}$ trimers, but also for the displacement of the double bond of 1-butene accompanied with the resultant conversion of the major part of 1-butene to 2-butenes, to obtain, with the selected catalysts and operating conditions, a composition close to that corresponding to the thermodynamic equilibrium. The other constituents of the charge are substantially unconverted during the isomerization reaction. This conversion of 1-butene to 2-butenes is essential to the alkylation reaction effected after fractionation of the isomerization effluent, since the products obtained by alkylation of the 2-butenes have a substantially higher octane number than the alkylates obtained from 1-butene (The alkylates obtained from 2-butene have a R.O.N. 5 to 7 units higher than that obtained when starting from 1-butene).

The process conforming to the invention, in the case of a charge recovered from catalytic cracking (usually having a rather high isobutane content), yields a typical feed charge for the unit where 2-butene is alkylated with isobutane, which means that the alkylation charge can be very often used as such in an alkylation unit, without (or with negligible) external supply of isobutane.

BRIEF DESCRIPTION OF THE DRAWING

The process conforming to the invention is illustrated by the single FIGURE of the accompanying drawing.

DETAILED DISCUSSION

The $C_4$ olefinic cut, which usually comprises isobutane, n-butane, 1-butene, 2-butenes, isobutene and a low or nil proportion of butadiene (generally less than 2% and preferably less than 0.7% b.w. of butadiene) can be optionally introduced at first through duct 1 into a drying zone 2. This drying is effected conventionally, for example by passing the cut through a molecular sieve, preferably a sieve of the 3 A type. The dried cut is fed through duct 3 to a selective polymerization zone 4 where isobutene of said cut is converted essentially to isobutene dimers and trimers.

In the polymerization zone, the conditions allow isobutene to react up to conversion rates higher than 95% b.w., and even higher than 96%, whereas the overall conversions of the normal butenes (1-butene and cis and trans 2-butenes) remain not in excess of 3% b.w., preferably lower than 2% or even lower than 1%.

The polymerization reactions are generally effected in the presence of a catalyst, arranged for example, as a fixed bed, at a temperature of about 30° to 400° C., under a pressure of about 0.1 to 20 MPa (1 to 200 bars); preferably the temperature is about 100° to 140° C., the pressure 3 to 5 MPa and the liquid hydrocarbon feed rate (space velocity) about 0.05 to 5 volumes per volume of catalyst per hour, preferably 0.8 to 2.5.

The catalyst of acid type may be silica-alumina, boron-alumina or boron-containing alumina. The selected catalyst may also be that obtained by treating transition alumina with an acid fluorine derivative, with optional addition of a silicic ester. The catalysts which are used, according to the present invention, in the polymerization reaction behave better than other polymerization catalysts, such as phosphoric acid on Kieselguhr, silica or quartz, or such as catalysts of the "solid phosphoric acid" type, i.e. catalysts consisting of a siliceous material with high adsorption capacity, impregnated with a substantial proportion of phosphoric acid, or even catalyst such as mixtures of alumina gel with thoria, either co-precipitated or not, with optional addition of chromium oxide, zinc oxide or an equivalent metal oxide.

A preferred silica-alumina for use in the present invention has a silica content of 60 to 95% b.w., preferably 70 to 90% and preferably further contains, as additive, from 0.1 to 5% b.w. of zinc oxide.

At the outlet of the polymerization zone 4, the whole effluent is fed through duct 5 directly to the butene hydroisomerization zone 6, without intermediate fractionation. In another arrangement of the process of the invention the same reactor is used to effect the isobutene polymerization and the butenes isomerization: the single reactor has in this case two catalyst beds, one for polymerization, the other for isomerization, these two distinct beds being then generally superposed. In that case, duct 5 is omitted. As shown in the drawing, the hydrogen required for the isomerization reaction is supplied through duct 7. In the case of a single reactor, hydrogen is supplied at the upper level of the isomerization catalyst bed.

The isomerization is effected in the presence of a catalyst arranged, for example, as a fixed, moving or fluidized bed, depending on the case, at a temperature between about 0° and 250° C., preferably between 100° and 140° C., under a pressure of about 0.1 to 20 MPa, preferably 3 to 5 MPa and at a liquid hydrocarbon feed rate of about 0.2 to 20 volumes of hydrocarbon per volume of catalyst per hour, preferably 1 to 3. The catalyst generally comprises at least one metal of group VIII from the periodic Table of elements, for example, cobalt, nickel, palladium, etc., carried on a support of low acidity, for example transition alumina, silica, etc of specific surface from about 20 to 300 $m^2$ per gram and pore volume from about 0.20 to 0.80 $cm^3$ per gram.

The acidity of the carrier may be determined by the known test of ammonia adsorption, as disclosed in Journal of Catalysis, 2, 211-222 (1963): the method consists of heating the carrier at 600° C. under vacuum (thus at a pressure lower than about 1 Pa) up to total gas removal; the carrier is then placed in a calorimeter at 320° C. and ammonia is introduced in such an amount that the final pressure of the balanced system amounts to 40 kPa, and the released heat is measured.

The carriers which are used have a neutralization heat, by ammonia adsorption, lower than 10 cal per gram at 320° C. under a pressure of 40 kPa, and preferably lower than 7 cal per gram. The neutralization heat of the final catalyst is practically the same, thus lower than 10 cal per gram and preferably lower than 7 cal per gram.

The catalyst can work in sulfurized medium (to inhibit the hydrogenating properties of the metal) or not. Loss of catalytic properties of the solid and secondary reactions are avoided by conducting the reaction under a partial pressure of hydrogen, which hydrogen can be supplied with the feed charge. The hydrogen/hydrocarbon ratio is then usually comprised between 0.01 and 2 (a ratio expressed in molecules per molecule).

In view of the high heat evolution of the polymerization conversion in zone 4, the isobutene content of the charge is preferably not higher than about 35% by weight; since otherwise it must be diluted with, for example, butane or isobutane and/or with a fraction or the totality of the butane and/or isobutane recovered, through the ducts 17 and 18, from the effluent of the alkylation zone 15, as hereinafter defined. This recycled butane and/or isobutane fraction is supplied either to the polymerization zone 4, when the polymerization reactor 4 is independant from the reactor (the case of the drawing), or to the inlet of the single reactor in the case of a single reactor with two distinct beds, one for polymerization and the other for isomerization.

The dilution can also be effected with fresh isobutane (and/or butane) introduced through the ducts 19 and 18.

In the course of the isomerization reaction, the 2-butene content of the feed charge increases: the operation is so conducted as to convert, in the course of the isomerization (hydroisomerization), at least 90% of 1-butene to 2-butenes, and as to obtain, in the effluent of the isomerization (hydroisomerization) zone, normal butenes consisting of at least 92% b.w. (preferably more than 93%) of 2-butenes and less than 8% b.w. (preferably less than 7%) of 1-butene.

It is sometimes preferred that the temperatures, pressures and VVH, together or separately, be approximately the same in the hydro-isomerization and polymerization reaction zones.

At the outlet from the isomerization zone, the whole reaction mixture, i.e. butenes, unreacted isobutene, isobutene dimers and trimers, butane and optional dilution butane, isobutane and optional dilution isobutane, etc., is supplied through line 8 to a fractionation zone 9 wherefrom are discharged, through duct 11, a first fraction mainly comprising butane, isobutane, isobutene and butenes, and through duct 10, a second fraction essentially comprising the isobutene dimers and trimers (polymerizate) which can be fed directly to the gasoline pool, any other fractionation and/or total or partial hydrogenation being generally unnecessary due to the quality of said polymerizate.

The fraction discharged through duct 11 from the fractionation zone 9 is fed to the alkylation zone 12.

As a rule, the alkylation reaction is effected either in the presence of a dissolved catalyst, i.e. in liquid phase, or in the presence of a solid catalyst, preferably used as a fixed bed, at a temperature from −20° to 200° C. and under a pressure of from 10 kPa to 20 MPa. It is thus possible to operate in liquid phase in the presence of a strong inorganic acid such as hydrofluoric acid or sulfuric acid with or without addition of a Lewis acid such as boron trifluoride or antimony pentafluoride, or even aluminum trichloride, and/or in the presence, if desired, of a Brönsted acid. It is possible to operate in vapor phase in the presence of a solid catalyst of the polyvalent metal phosphates, arsenates or stannates type, together with boron trifluoride. Other alkylation processes are operated in the presence of catalysts having a zeolitic sutructure, with a molecular sieve, with or without silica-alumina, optionally with at least one metal such as nickel, palladium, rhodium, platinum, etc.

More particularly, the alkylation reaction can be effected at temperatures close to room temperature and at moderate pressures.

Additional isobutane (and/or butane) can be supplied through the ducts 16, 17 and 13 (and/or 19 and 13) to the alkylation zone 12, in order to maintain an adequate isobutane/olefins molar ratio of from about 1/1 to 10/1 at the inlet of the alkylation zone, which ratio provides for an alkylate with an optimum octane number.

The alkylation provides an alkylate which is withdrawn through duct 14 and can be fractionated in zone 15, to obtain:

(a) a fraction, discharged through duct 16, usually comprising saturated hydrocarbons (iso and normal paraffins) with 4 carbon atoms per molecule, thus butanes of high isobutane content which can be supplied, according to the case, to the polymerization zone 4 through lines 17 and 18 (on the FIGURE, line 18 opens at the inlet of the isomerization zone, as explained above), so as to avoid any excessive temperature increase, and/or to the alkylation zone 12 through duct 13, and (b) an alkylate useful, for example, as motor fuel since the alkylation products have generally a clear octane number of from 88 to 95. This alkylate is recovered through duct 21 and is usually admixed with the polymerizate of line 10, according to a preferred embodiment of the invention.

Additional isobutane for optional dilution of the charge (duct 1) and the cut (duct 13) fed to the alkylation zone can be supplied through duct 19.

EXAMPLE 1

By way of example, an olefinic $C_4$ cut is treated after extraction of butadiene; the composition of the charge is given in Table I.

TABLE I

| Composition of the feed charge (% by weight) | |
| --- | --- |
| Isobutane | 1.3 |
| N—butane | 6.4 |
| 1-butene | 27.9 |
| 2-butenes | 14.5 |
| Isobutene | 49.6 |
| Butadiene | 0.3 |

The charge is first subjected to drying on a molecular sieve 3 A and thereafter treated in an isomerizing polymerization zone, i.e. a zone consisting of two successive fixed catalyst beds; the first one, where the polymerization takes place, contains as catalyst silica-alumina of the trade, of the Durabead Perl Catalysator Neu type sold by Kalichemie Company, further containing 0.2% b.w. of zinc.

The second bed, where the isomerization takes place, contains an LD 265 catalyst of the trade, sold by Procatalyse Company; this catalyst consists of highly pure alumina with 0.3% b.w. of palladium. Its specific surface is 60 m²/g, its pore volume 0.5 cc/g and its bulk density 0.7 g/cc. It is sold as 2 to 4 mm balls. The neutralization heat of this catalyst, determined in the above stated conditions is 6 cal. per gram.

The operating conditions, in each of the two isomerization and polymerization zones are as follows:

| Polymerization: | | Isomerization: | |
| --- | --- | --- | --- |
| VVH(h$^{-1}$) | 1 | VVH(h$^{-1}$) | 2 |
| T °C. | 120 | T °C. | 120 |
| Pressure MPa | 4 | Pressure MPa | 4 |
| | | H$_2$/HC | 0.5 |

The composition of the effluent at the outlet of the polymerization zone and the composition of the effluent at the outlet of the isomerization zone are given in the following Table II. The compositions are given with respect to the initial charge.

TABLE II

| | POLYMERIZATION EFFLUENT % b.w. | ISOMERIZATION EFFLUENT % b.w. |
| --- | --- | --- |
| Isobutane | 1.3 | 1.3 |
| N—butane | 6.4 | 6.4 |
| 1-butene | 27.8 | 2.5 |
| 2-butenes | 14.5 | 39.8 |
| Isobutene | 1.4 | 1.4 |

TABLE II-continued

| | POLYMERIZATION EFFLUENT % b.w. | ISOMERIZATION EFFLUENT % b.w. |
| --- | --- | --- |
| C$_8$-C$_{12}$ cuts (polymerizate) | 48.6 | 48.6 |

After fractionation of the isomerization effluent in zone 9 of the FIGURE, a fraction is recovered through duct 11 from the top of the column, whose composition in % b.w. with respect to the initial charge is:

| Isobutane: | 1.3% | |
| --- | --- | --- |
| N—butane: | 6.4% | |
| 1-butene: | 2.5% | |
| 2-butenes: | 39.8% | } 42.3% |
| Isobutene: | 1.4% | |

Gasoline is recovered through duct 10 from the bottom of the column; it represents 48.6% b.w. of the initial charge and has the following properties:

| sp. grav. at 15° C.: | 0.752 |
| --- | --- |
| octane numbers | |
| RON clear: | 101 |
| RON 0.5% ethylated: | 104.5 |
| MON clear: | 84 |
| MON 0.5% ethylated: | 87 |
| distillation ASTM | |
| IP: | 80° C. |
| 5%: | 108 |
| 10%: | 110 |
| 20%: | 115 |
| 30%: | 123 |
| 40%: | 132 |
| 50%: | 143 |
| 60%: | 160 |
| 70%: | 171 |
| 80%: | 178 |
| 90%: | 185 |
| 95%: | 193 |
| 98%: | 215 |
| FP: | 250 |
| distillate: | 99.5 |
| residue: | 0.5 |
| loss: | — |

This gasoline can be fed to the gasoline pool without being subjected to another fractionation or purification step (for example, by hydrogenation).

The fraction from duct 11, containing normal butane, isobutane, isobutene and 1- and 2-butenes, is supplied to the alkylation zone 12. However, in this cut, the amount of isobutane is insufficient (1.3% of isobutane for 42.3% of butenes by weight with respect to the initial charge) to provide an isobutane/olefins ratio avoiding undesirable secondary reactions. An amount of isobutane representing 44.6% b.w. of the initial charge of duct 1 is added through duct 13. The isobutane can be, for example, excess isobutane recovered in ducts 16, 17 and 13 and/or fresh isobutane introduced through column 19.

The alkylation reaction is effected in the presence of hydrofluoric acid, in reactor 12 which is stirred and cooled to maintain a temperature of 30° C. in the reaction mixture. The other operating conditions are as follows:

pressure: 1.5 MPa
volume of hydrofluoric acid (85% b.w.) per hour and per volume unit of olein: 2
acid/hydrocarbons ratio by volume: 1

The effluent from the alkylation zone 12, withdrawn through duct 14, is then fractionated in zone 15. There is thus recovered, on the one hand, through duct 16, excess isobutane and butane representing 6.4% b.w. of the total initial charge of duct 1, and, on the other hand, through duct 21, a gasoline alkylate representing 89.1% b.w. of the total initial charge of duct 1.

Isobutane and/or butane can be fed back at least partly to (polymerization) zone 4 through ducts 17 and 18 or discharged through duct 20.

The RON and MON of the "poly" gasoline (polymerizate of duct 10), of the alkylate of duct 21 and of the mixture of "poly" gasoline with alkylate are given in Table III.

TABLE III

|  | RON | RON ETHYLATED (0.5°/oo Pb) | MON | MON ETHYLATED (0.5°/oo Pb) |
|---|---|---|---|---|
| Alkylate | 95 | 108.5 | 92 | 107.0 |
| "Poly" gasoline | 101 | 104.5 | 84 | 87 |
| Mixture of alkylate with "poly" gasoline | 97.5 | 107.6 | 89.5 | 100.3 |

The octane numbers of the mixture show a synergistic effect between the constituents of the mixture since the theoretical octane numbers of this mixture are as follows:

RON:

$$95 \times \frac{89.1}{89.1 + 48.6} + 101 \times \frac{48.6}{89.1 + 48.6} = 97.11$$

RON ethylated $$108.5 \times \frac{89.1}{89.1 + 48.6} + 104.5 \times \frac{48.6}{89.1 + 48.6} = 107.08$$

MON $$92 \times \frac{89.1}{89.1 + 48.6} + 84 \times \frac{48.6}{89.1 + 48.6} = 89.17$$

MON ethylated $$107.0 \times \frac{89.1}{89.1 + 48.6} + 87 \times \frac{48.6}{89.1 + 48.6} = 99.93$$

It is thus advantageous to recover the mixture of the alkylate with the "poly" gasoline.

EXAMPLE 1 A (comparison)

The fresh charge of example 1 is fed directly to the alkylation zone 12, without intermediate polymerization and isomerization. In example 1, it was necessary to feed the alkylation zone 12, through duct 13, with 44.6% of isobutane by weight with respect to the initial charge.

It is here necessary to feed 96.5% of isobutane (by weight of the initial charge) through duct 13: this shows that the process of the invention reduces the requirements of isobutane in the alkylation unit, thus decreasing the cost of the resultant alkylates. The excess of isobutane and butane, amounting to 6.4% b.w. of the initial charge, is recovered in line 16. The alkylate is recovered in duct 21; it amounts to 189.9% b.w. of the initial charge and has the following octane numbers (not so high as in example 1):

| RON | ethylated RON (0.5°/oo Pb) | MON | ethylated MON (0.5°/oo Pb) |
|---|---|---|---|
| 93 | 105.5 | 90 | 105 |

EXAMPLE 2

An olefinic catalytic cracking C$_4$ cut is treated in the same apparatus as in example 1, under the same conditions and with the same catalysts as in example 1 for example 1 for each of the concerned reactions: polymerization, hydroisomerization and alkylation.

The composition of this cut in % b.w. is as follows (after extraction of butadiene):

| isobutane | 35 |
|---|---|
| n-butane | 12 |
| 1-butene | 10 |
| 2-butenes | 27 |
| isobutene | 16 |
| butadiene | 0 |
|  | 100 |

The charge is first dried on a 3 A molecular sieve and then treated in an isomerizing polymerization zone, thus in a zone comprising two successive fixed beds of catalyst; the polymerization reaction is effected in the first bed with the catalyst of example 1; the isomerization reaction is effected in the second bed with the catalyst of example 1.

Table IV gives the composition of the effluent at the outlet of the polymerization zone and the composition of the effluent at the outlet of the isomerization zone. The compositions are given in % b.w. of the initial charge.

TABLE IV

|  | POLYMERIZATION EFFLUENT % b.w. | ISOMERIZATION EFFLUENT % b.w. |
|---|---|---|
| Isobutane | 35 | 35 |
| n-butane | 12 | 12 |
| 1-butene | 9.9 | 0.9 |
| 2-butenes | 27 | 36 |
| isobutene | 0.5 | 0.5 |
| polymerizate gasoline (C$_8$ to C$_{12}$) | 15.6 | 15.6 |

After fractionation of the isomerization effluent in zone 9 of the FIGURE, a fraction is recovered through line 11 from the top of the column, which fraction has the following composition in % b.w. of the initial charge:

| isobutane: | 35% |  |
|---|---|---|
| n-butane: | 12% |  |
| 1-butene: | 0.9% | ⎫ |
| 2-butenes: | 36% | ⎬ 36.9% |
| isobutene: | 0.5% | ⎭ |

Gasoline (polymerizate) is recovered through duct 10 from the bottom of the column; it amounts to 15.6% b.w. of the initial charge and has substantially the same properties as the polymerizate obtained in example 1. Thus, the octane numbers are as follows:

| RON clear: | 101 |
|---|---|
| RON ethylated with 0.5°/$_{oo}$ Pb: | 104.5 |
| MON clear: | 84 |
| MON ethylated with 0.5°/$_{oo}$ Pb: | 87 |

This gasoline can be fed to the gasoline pool without being subjected to another fractionation or purification step (for example, by hydrogenation).

The fraction from duct 11, which contains normal butane, isobutane, isobutene and 1- and 2-butenes is thus supplied to the alkylation zone 12. Here, contrary to example 1, the amount of isobutane is practically sufficient (35% of isobutane for 36.9% of butenes b.w. of the initial charge) to obtain the isobutane/olefins ratio necessary to avoid undesirable secondary reactions. However, there is added through duct 13 a small amount of isobutane representing 4.2% b.w. of the initial charge of duct 1. Isobutane can be, for example, isobutane in excess recovered through ducts 16, 17 and 13 and/or fresh isobutane introduced through duct 19.

The effluent of the alkylation zone 12 is then fractionated in zone 15 and withdrawn through duct 14. There is thus obtained, on the one hand, through duct 16, the excess of isobutane and butane which represents 12% b.w. of the total initial charge of duct 1, and, on the other hand, through duct 21, a gasoline alkylate representing 76.2% b.w. of the total initial charge of duct 1.

Table V gives the RON and MON obtained with the "poly" gasoline (polymerizate of duct 10), the alkylate of duct 21 and the mixture of the "poly" gasoline with alkylate:

TABLE V

|  | RON | RON ETHYLATED (0.5°/$_{oo}$ Pb) | MON | MON ETHYLATED (0.5°/$_{oo}$ Pb) |
|---|---|---|---|---|
| Alkylate | 95 | 109 | 92 | 107 |
| "Poly" gasoline | 101 | 104.5 | 84 | 87 |
| Mixture of alkylate with "poly" gasoline | 96.6 | 108.8 | 91.1 | 104 |

The octane numbers of the mixture show a synergic effect between the constituents of the mixture since the theoretical octane numbers of this mixture are as follows:

RON:
$$95 \times \frac{76.2}{76.2 + 15.6} + 101 \times \frac{15.6}{76.2 + 15.6} = 96.01$$

RON ethylated:
$$109 \times \frac{76.2}{76.2 + 15.6} + 104.5 \times \frac{15.6}{76.2 + 15.6} = 108.23$$

MON:
$$92 \times \frac{76.2}{76.2 + 15.6} + 84 \times \frac{15.6}{76.2 + 15.6} = 90.64$$

MON ethylated:
$$107 \times \frac{76.2}{76.2 + 15.6} + 87 \times \frac{15.6}{76.2 + 15.6} = 103.60$$

It is thus advantageous to recover both the alkylate and the polymerizate gasoline.

EXAMPLE 2 A (comparison)

The fresh charge of example 2 is supplied directly to the alkylation zone 12 without intermediate polymerization and isomerization. In example 3, it was sufficient to supply 4.2% of isobutane, by weight of the initial charge, to the alkylation zone 12 through duct 13. It is now necessary to supply 20.9% of isobutane, by weight of the initial charge, through duct 13: this shows that, as in example 1 (a charge from steam-cracking), the process conforming to the invention saves isobutane in the alkylation unit; it decreases the cost of the resultant alkylates. The isobutane and butane excess, representing 12% b.w. of the initial charge, is recovered in duct 16. The alkylate, amounting to 108.6% b.w. of the initial charge, is recovered in duct 21; it has the following octane numbers (not as good as in example 3):

| RON | ethylated RON (0.5°/$_{oo}$ Pb) | MON | ethylated MON (0.5°/$_{oo}$ Pb) |
|---|---|---|---|
| 94 | 107 | 91 | 106 |

EXAMPLE 1 B (comparison)

The charge of example 1 is treated; however the hydroisomerization zone 6 is no longer used. In other words, the charge passes directly from the polymerization zone 4 to the fractionation zone 9 without supply of hydrogen required for hydro-isomerization. The other operating conditions remain unchanged. The results are given hereunder in relation with the whole charge of duct 1. The results of example 1 are given in parentheses.

| alkylate: | 86.0% (89.1%) |
|---|---|
| polymerization: | 48.6% (48.6%) |

Table VI gives the octane numbers of the resultant products (in parentheses are the octane numbers obtained in example 1):

TABLE VI

|  | RON | RON ETHYLATED (0.5°/$_{oo}$ Pb) | MON | MON ETHYLATED (0.5°/$_{oo}$ Pb) |
|---|---|---|---|---|
| Alkylate | 92.5 (95) | 105.5 (108.5) | 90 (92) | 105 (107) |
| Polymerizate gasoline | 101 (101) | 104.5 (104.5) | 84 (84) | 87 (87) |
| Mixture of alkylate with polymerizate gasoline | 95.4 (97.5) | 105.2 (107.6) | 84.9 (89.5) | 98.6 (100.3) |

The octane numbers of the mixtures are not as good as the theoretical octane numbers calculated in example 1. It would also be necessary to hydrogenate the polymerizate gasoline to improve its properties.

EXAMPLE 2 B (comparison)

The charge of example 2 is treated, but the hydro-isomerizaton zone 6 is not used. In other words, the charge passes directly from the polymerization zone 4 to the fractionzation zone 9.

The other operating conditions are unchanged. The results are given hereunder with respect to the whole charge of duct 1. The results of example 1 are given in parentheses.

| | |
|---|---|
| alkylate: | 76.1 (76.2) |
| polymerizate: | 15.5 (15.6) |

The resultant gasolines, which can be used as motor fuels, have the following octane numbers given in Table VII (in parentheses are: the octane numbers obtained in example 2):

TABLE VII

| | RON | RON ETHYL-ATED (0.5‰ Pb) | MON | MON ETHYL-ATED (0.5‰ Pb) |
|---|---|---|---|---|
| Alkylate | 94 (95) | 108 (109) | 91.5 (92) | 106.5 (107) |
| Polymerizate gasoline | 101 (101) | 104.5 (104.5) | 84 (84) | 87 (87) |
| Mixture of alkylate with polymerizate gasoline | 95.5 (96.6) | 107.5 (108.8) | 90.4 (91.1) | 102.5 (104) |

Here the octane numbers of the mixtures are not as good as the theoretical octane numbers calculated in example 2. It would also be necessary to hydrogenate the polymerizate gasoline to improve its properties.

What is claimed is:

1. A process for upgrading a dried $C_4$ olefinic cut, obtained from a cracking unit or a steam-cracking unit, substantially freed of butadiene, and dried, said process comprising the steps of:
   (a) feeding the dried $C_4$ cut to a selective catalytic polymerization zone in the presence of a polymerization catalyst, said catalyst being a fluorinated alumina, a boron-alumina or a silica-alumina, and converting at least 95% of the isobutene of said olefinic cut, in major part to isobutene dimers and trimers, while limiting the overall conversions of the normal butenes of said starting olefinic cut to not over 3% by weight, the butane and isobutane of said olefinic cut being substantially unconverted;
   (b) feeding the effluent from the polymerization zone to a hydroisomerization zone, in the presence of hydrogen and an isomerization catalyst comprising at least one Group VIII metal deposited on a carrier, and isomerizing the polymerization effluent under such conditions that at least 90% of the 1-butene of said polymerization effluent is isomerized to 2-butenes, the percentages of the other constituents of said effluent remaining substantially unchanged, the proportions of the normal butenes in the hydroisomerization effluent at the end of the isomerization reaction being at least 92% by weight of 2-butenes and less than 8% by weight of 1-butene;
   (c) fractionating the effluent from the isomerization zone, and separately recovering a bottoms poly gasoline fraction comprising, in major part, isobutene dimers and trimers, and an overhead fraction comprising, in major part, isobutane, butane and butenes; and
   (d) feeding the overhead fraction to an alkylation zone, fractionating the alkylation effluent, and separately recovering an overhead fraction of high saturated $C_4$ hydrocarbon content, and an alkylate.

2. A process according to claim 1, which further comprises combining the alkylate from step (d) with the poly gasoline fraction from step (c), and recovering the resultant combined fractions as gasoline.

3. A process according to claim 1, wherein the catalyst which is used in the hydro-isomerization zone has a neutralization heat by ammonia adsorption lower than 10 calories per gram at 320° C. and 40 kPa.

4. A process according to claim 3, wherein the catalyst carrier in the hydro-isomerization zone is alumina and the Group VIII metal of said catalyst is cobalt, nickel or palladium.

5. A process according to claim 4, wherein the metal is palladium.

6. A process according to claim 1, wherein the polymerization reaction is effected at a temperature between 30° and 400° C., under a pressure of about 0.1 to 20 MPa, at a liquid hydrocarbon feed rate of about 0.05 to 5 volumes of catalyst per hour, and wherein the hydroisomerization reaction is effected at a temperature between 0° and 250° C., under a pressure of about 0.1 to 20 MPa, at a liquid hydrocarbon feed rate of about 0.2 to 20 volumes of hydrocarbon per volume of catalyst per hour.

7. A process according to claim 6, wherein the polymerization reaction is effected at a temperature between 100° and 140° C., under a pressure of 3 to 5 MPa, and wherein the hydroisomerization reaction is effected at a temperature between 100° and 140° C. under a pressure of 3 to 5 MPa.

8. A process according to claim 1, wherein the polymerization catalyst and the hydroisomerization catalyst are disposed in the same reaction zone, as superposed beds; wherein, in the course of step (a), at least 96% of isobutene is converted in major part to isobutene dimers and trimers, while limiting the overall conversions of the normal butenes of said starting olefinic cut to lower than 2%; and wherein the normal butenes in the effluent from the isomerization zone are present in the proportions of at least 93% of 2-butenes and less than 7% of 1-butene.

9. A process according to claim 8, wherein the temperatures and pressures are substantially the same for the polymerization and hydroisomerization reactions.

* * * * *